United States Patent [19]

Taniguchi et al.

[11] Patent Number: 5,149,436

[45] Date of Patent: * Sep. 22, 1992

[54] CONTINUOUS DISPLACEMENT CHROMATOGRAPHIC METHOD

[75] Inventors: Vernon T. Taniguchi, Anaheim; Allen W. Doty, Pomona, both of Calif.

[73] Assignee: Union Oil Company of California, Los Angeles, Calif.

[*] Notice: The portion of the term of this patent subsequent to Apr. 10, 2007 has been disclaimed.

[21] Appl. No.: 782,816

[22] Filed: Oct. 25, 1991

Related U.S. Application Data

[60] Continuation of Ser. No. 434,913, Nov. 8, 1989, abandoned, which is a division of Ser. No. 276,627, Nov. 28, 1988, Pat. No. 4,915,843.

[51] Int. Cl.$^5$ ............................................. B01D 15/08
[52] U.S. Cl. ............................ 210/657; 210/656; 210/659; 210/198.2
[58] Field of Search ............... 210/635, 656, 657, 659, 210/198.2; 55/67, 386

[56] References Cited

U.S. PATENT DOCUMENTS

| | | | |
|---|---|---|---|
| 3,062,739 | 11/1962 | Crits | 210/672 |
| 3,511,028 | 0/1970 | Saylor | 55/67 |
| 3,732,982 | 0/1973 | Dunnill et al. | 210/198 C |
| 3,869,536 | 3/1975 | James | 423/7 |
| 3,971,842 | 7/1976 | Ewbank | 423/7 |
| 4,042,350 | 8/1977 | Phillips | 55/28 |
| 4,172,185 | 10/1979 | Petheram | 210/673 |
| 4,276,060 | 6/1981 | Aldridge | 55/67 |
| 4,411,793 | 10/1983 | Kato et al. | 210/656 |
| 4,412,866 | 11/1983 | Schoenruck | 210/656 |
| 4,500,430 | 2/1985 | Dasgupton | 210/656 |
| 4,528,101 | 7/1985 | Burke | 210/656 |
| 4,599,175 | 7/1986 | Yamamizu et al. | 210/635 |
| 4,600,566 | 7/1986 | Fujine et al. | 423/179.5 |
| 4,849,110 | 7/1989 | Takata | 210/656 |
| 4,915,843 | 4/1990 | Taniguchi | 210/659 |

FOREIGN PATENT DOCUMENTS

| | | | |
|---|---|---|---|
| 2440848 | 3/1976 | Fed. Rep. of Germany | 210/659 |
| 2065495 | 7/1981 | United Kingdom | 210/659 |

OTHER PUBLICATIONS

Snyder, Introduction to Modern Liquid Chromatography, John Wiley & Sons, Inc. 1979, New York, pp. 173-184 & 238-240.

Begovich, John M., et al., "A High-Capacity Pressurized Continuous Chromatograph", Separation Science and Technology, 18 (12 & 13), pp. 1167-1191, (1983).

Begovich, J. M., et al., "Continuous Ion Exchange Separation of Zirconium and Hafnium Using an Annular Chromatograph", *Hydrometallugy*, 10 (1983), pp. 11-20.

Begovich, J. M. et al., "A Rotating Annular Chromatograph for Continuous Separations", *AIChE Journal*, (vol. 30, No. 5), Sep. 1984, pp. 705-710.

Canon, R. M., et al., "Pressurized Continuous Chromatography", *Separation Science and Technology*, 15(3), pp. 655-678, (1980).

Canon, R. M., et al., "Operation of an Improved, Continuous Annular Chromatograph", *Journal of Liquid Chromatography*, 1(4), pp. 427-441 (1978).

Choppin, G. R., et al., "Ion Exchange Studies of Alpha-Hydroxy Carboxylic Acid-Lanthanide and Actinide Systems", *Radioisotopes in the Physical Sciences & Industry; Proc. of a Conference*, vol. 3, pp. 283-299, Ion Exchange Studies (1962).

Cuninghame, J. G. et al., "The Rapid Separation of Rare-earth Fission Products by Cation Exchange, using Lactic-acid Eluant", *J. Inorg. Nucl. Chem.*, 1955, 1, 163-164.

(List continued on next page.)

Primary Examiner—Ernest G. Therkorn
Attorney, Agent, or Firm—Gregory F. Wirzbicki; Shlomo R. Frieman

[57] ABSTRACT

Chromatographic species are continuously separated by displacement chromatography using an apparatus that comprises an inlet distribution manifold, a particulate bed, and a plurality of collector receptacles. The particulate bed is moved with respect to the inlet distributor manifold and the collector receptacles.

20 Claims, 3 Drawing Sheets

OTHER PUBLICATIONS

Frieling, E. C., et al., "Ion Exchange as a Separations Method VII. near Optimum Conditions for the Separation of Fission Product Rare Earths with Lactic Acid Eluant at 87°"', *JACS*, 1954, 76, 1021–1022.

Holm, L. W., et al., "Negative Chelate Complexes of Lanthanide and Actinide Elements", *J. Inorg. Nucl. Chem.*, 1961, vol. 19, pp. 251–261.

Howard, A. J., et al., "Separation of Sugars by Continuous Annular Chromatography", Issued Aug. 1987 as a thesis, prepared by ORNL ORNL/TM-10318, pp. iii–63.

Johnson, E. L., et al., "II. Column Theory", *Basic Liquid Chromatography*, pp. 15–51 (1978).

Kirk-Othmer Encyclopedia of Chemical Technology, vol. 19, Third Edition, pp. 842–847 (1982).

Korkisch, Johann, "Modern Methods for the Separation of Rarer Metal Ions", pp. 201–214 (1966).

Martin, A. J. P., "Summarizing Paper", *Chromatographic Analysis*, No. 7, (1949), pp. 332–336.

Mayer, S. W., et al., "Ion Exchange as a Separation Method. VI. Column Studies of the Relative Efficiencies of Various Complexing Agents for the Separation of Lighter Rare Earths", *JACS*, 1953, 75, 5647–5649.

Nervik, W., "An Improved Method for Operating Ion-Exchange Resin Columns in Separating the Rare-Earth Elements", *J. Phys. Chem.* 1955, 59, 690–695.

Powell, J. E., "The Separation of Rare Earths by Ion Exchange", vol. 1, Progress in the Science and Tech. of Rare Earths L. Eyring, ed. Pergamon Press (1964) pp. 62–83.

Powell, J. E., "Basic Principles Involved in the Macroseparation of Adjacent Rare Earths from Each Other by Means of Ion Exchange", *Chem. Eng. Prog.*, 1959, 55, pp. 101–113.

Powell, J. E., et al., "The Separation of Rare Earths by Ion Exchange", *Trans. of The Metallurgical Society of AIME*, vol. 215, Jun. 1959, pp. 457–463.

Powell, J. E., et al., "The Separation of Rare Earths", *J. of Chem. Ed.*, vol. 37, No. 12, Dec. 1960, pp. 629–633.

Scott, C. D., et al., "Pressurized, Annular Chromatograph for Continuous Separations", *J. of Chromatography*, 126 (1976) pp. 381–400.

Powell, J. E., "Separation of Rare Earths by Ion Exchange", *The Rare Earths*, Chap. 5, (1971), pp. 55–73.

Spedding, F. H., et al., "The Stability of the Rare Earth Complexes with N-Hydroxyethylethylenediaminetriacetic Acid", *JACS*, vol. LXXVIII, Jan.-Mar. 1956, pp. 34–37.

Streat, "The Use of Gradient Elution in Optimizing Continuous Annular Ion Exchange Chromatography with Applications to Metal Separations", *Ion Exchange for Industry*, (1988), pp. 424–442.

Fujine et al., *Separation Science and Technology*, 17:1545–1563 (1982–1983).

Sisson et al., "Chromatography", *Chemtech*, Aug. 1988, pp. 498–502.

Arohart et al., *Chemical Eng'g. Progress*, 52 (9):353–359 (1956).

Barker et al., *Separation Science and Technology*, 22, (8-10):2011–2035 (1987).

Dunnill et al., *Biotechnol. & Bioeng. Symp. No. 3*, pp. 97–113 (1972).

Fox, *J. of Chromatog.*, 43:55–60 (1969).

Fox et al., *J. Chromatog.*, 43:48–54 (1969).

Giddings, *Analytical Chemistry*, 34(1):37–39 (1962).

Nicholas et al., *J. Chromatog.*, 43:61–65 (1969).

Svensson et al., *Science Tools*, 2:17–21 (1955).

Yoshisato et al., *Separation Science and Technology*, 21(8):727–753 (1986).

Taniguchi et al., *Journal of Metals*, 40(11):p. 56, Annual Meeting, (Nov. 1988).

De Carli et al., Displacement Separation by Continuous Annular Chromatography, Extended Abstracts, American Institute of Chemical Engineers, 1988 Annual Meeting and BioChemE, Nov. 27, 1988 p. ID.

Multicomponent Separations by Continuous Annular Chromatography, Oak Ridge National Laboratory (Mar. 1987).

Proposal No. CHE-ORNL-3590-87 (Dec. 1986) (Entire Document).

Proposal No. CHE-ORNL-3882-88 (Nov., 1987) (Entire Document).

Mid-Atlantic Biochemical Engineering Consortium (MABEC) Second Annual Student Symposium (Feb., 1988) (Entire Document).

Multicomponent Separations by Continuous Annular Chromatography, Oak Ridge National Laboratory (Mar. 1988) (Entire Document).

CONTINUOUS DISPLACEMENT CHROMATOGRAPHIC METHOD

CROSS-REFERENCE TO RELATED APPLICATIONS

This application is a continuation of application Ser. No. 07/434,913, filed Nov. 8, 1989 now abandoned, which is a divisional of application Ser. No. 07/276,627, filed Nov. 28, 1988 (now U.S. Pat. No. 4,915,843), which applications are incorporated herein in their entireties by reference.

BACKGROUND

The present invention relates to displacement chromatography and displacement chromatographic apparatus.

Chromatography is a method for separating components from a mixture of chemical substances. It is particularly useful with mixtures of compounds whose chemical or physical properties are so nearly identical as to make other separation techniques difficult or impractical. The various components are resolved by their selective retardation as they are transported through a bed of sorptive medium by a moving fluid. The separation of the components depends upon their relative affinity for the sorbent and the moving fluid, the length of the chromatographic device, and the fluid flow rate.

Four separate mechanisms or processes exist for retention of sample molecules by the stationary phase. These, in turn, give rise to four basic chromatographic methods, namely, liquid-liquid, liquid-solid, ion-exchange, and size-exclusion chromatography. Liquid-liquid or partition chromatography involves a liquid stationary phase whose composition is different from that of the liquid moving phase. Simple molecules distribute between the mobile and stationary liquid phases, just as in liquid-liquid extraction with a separatory funnel. The moving- and stationary-phase liquids must be immiscible. Liquid-solid or adsorption chromatography involves high-surface-area particles, with retention of sample molecules occurring by attraction to the surface of the particles. In ion-exchange chromatography, the stationary phase contains fixed ionic groups such as sulfonate ($-SO_3^-$) along with counter-ions of opposite charge, e.g., $Na^+$. The counter-ions are also normally present in the mobile phase in the form of a dissociated salt, e.g., NaCl. Simple ionic species, e.g., $X^+$, are retained by an ion exchange mechanism:

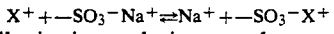

$$X^+ + -SO_3^-Na^+ \rightleftharpoons Na^+ + -SO_3^-X^+$$

Finally, in size-exclusion or gel permeation chromatography the column packing is a porous is a porous material with pores of a certain size. Molecules that are too large are excluded from all the pores, whereas small molecules can penetrate most of the pores. Thus, very large molecules move through the column quickly and smaller molecules are retained by the packing. Usually, separation in size-exclusion chromatography is determined strictly by molecular size.

Two additional chromatographic methods result from modification of liquid-liquid chromatography, namely, bonded-phase chromatography and ion-pair chromatography. Bonded-phase chromatography uses an organic stationary phase that is chemically bonded to the particles in place of the mechanically held liquid phase used in liquid-liquid chromatography. Ion-pair chromatography can be regarded as a combination of liquid-liquid chromatography or bonded-phase chromatography and ion-exchange chromatography. Ion-pair chromatography can be carried out with either a mechanically held liquid stationary phase or a bonded phase.

Within the four basic chromatography methods, at least two entirely different, distinct separation protocols exist. These have been named displacement chromatography and analytical or elution chromatography. In displacement chromatography at least two species B and C are sorbed onto the stationary phase or resin which was originally loaded with a third specie A having less affinity for the stationary phase than either B or C. Typically, up to 50 percent of the total capacity of the resin is loaded with species B and C. A displacer reagent consisting of a specie D is then passed through the resin. Specie D has an affinity for the resin greater than either B or C and causes the mixture of B and C (1) to be displaced from the resin, and (2) to segregate into bands of equal concentration that elute from the resin in a head-to-tail fashion.

In analytical or elution chromatography, the mixture to be separated is initially adsorbed on the stationary phase. An eluting species or eluent contained in the mobile, liquid phase is then passed through the resin. The eluent also has affinity for the components of the mixture which is different from the affinity of the components for the resin. The eluent need not have any affinity for the stationary resin phase. Separation is achieved by the competition of the stationary resin phase and the mobile eluent phase for the components in the mixture. The components are resolved into symmetrical Gaussian-shaped peaks that are separated on the resin to an extent determined by the resolution, selectivity, and efficiency of the system. The resin cannot be loaded to more than 1-5% of the total resin capacity with the mixture before resolution and peak symmetry are adversely affected.

Analytical or elution chromatography is designed to separate small quantities of a mixture to a very high degree of separation or resolution. It is therefore best suited and most widely used in small-scale analytical applications. It is not a method that lends itself readily to separation of large amounts of material.

Displacement chromatography, on the other hand, is a preparative technique that can separated 10 to 50 times the amount of material that can be processed by elution chromatography. Although resolution of the components is somewhat less, displacement chromatography is the method of choice for large-scale, industrial chromatographic separations.

In its conventional implementation, chromatography is a batch process. A volume of the mixture to be separated is introduced at the feed end of a chromatographic column (i.e., a single cylindrical tube filled with resin) and the components are resolved, in time, into individual bands along the column length. The separated components are then recovered at the column exit since they are eluted at different times.

Elution chromatography is applicable to many types of mixtures and has high resolution capabilities and high versatility, but its deficient throughput capacity and lack of continuous operation keep it from being a separation technique suitable for large scale, industrial operations. Attempts have been made to increase the capacity of chromatographic devices. One attempt is the continuous annular chromatography (CAC) system based upon elution and gradient elution chromatography.

Continuous chromatographic separations can be achieved by means of the CAC system. The CAC apparatus consists of an annular particulate bed having adsorbent particles packed in a space between two concentric cylinders. While the column assembly is slowly rotated about its axis, an eluent solution and a feed mixture are continuously fed to the annular bed. The eluent is uniformly fed to the entire circumference, but the feed mixture is introduced at only a fixed point on the circumference that remains stationary in space. As time progresses, helical component bands develop and separate from the feed point, with slopes dependent upon eluent velocity, rotational speed, and the distribution coefficient of the components. These bands are fixed in space and exit at separated, stationary exit points at the opposite end of the annular bed. As long as conditions remain constant, the angular position of each component band from the feed point also remains constant. No regeneration is required in CAC systems because the feed mixture is removed from the particulate bed by the eluent without changing the chemical make-up of the particulate bed. Hence, the CAC system is a continuous, steady-state process.

In the CAC system, the length and time coordinates characteristic of conventional chromatographic separation is replaced with the length and angle coordinates of the rotating bed. In this respect, conventional elution and gradient elution chromatography and elution and gradient elution CAC, respectively, are completely analogous. Therefore, elution and gradient elution CAC should be able to perform continuously any separation capable of being preferred by conventional batch elution and batch gradient elution chromatography.

Since only a small portion of the resin capacity, typically less than about 5 percent, can be loaded with the chromatographic species to be separated in both elution and gradient elution CAC, the CAC methodology nevertheless has a significant drawback in that it can only separate relatively small amounts of chromatographic species per unit volume of resin.

SUMMARY

The present invention provides a continuous chromatographic method wherein large amounts of chromatographic species are separated per unit volume of resin. More particularly, in the method of the instant invention, a feed mixture stream, a displacer reagent stream, and a barrier reagent stream are simultaneously introduced proximate one end of a particulate bed. Generally, these streams are introduced proximate the top end of the particulate bed. The particulate bed comprises a resin. The feed stream comprises a chromatographic mixture of at least two species B and C to be separated. C has a greater affinity than B for the resin. The displacer stream comprises a chromatographic specie D which has a greater affinity than C for the resin. The barrier stream comprises a chromatographic specie A having less affinity than B for the resin. The streams are moved with respect to the particulate bed so that substantially all the resin is sequentially contacted with (i) the feed mixture stream, (ii) the displacer reagent stream, and (iii) the barrier reagent stream. Substantially pure B and substantially pure C are separately collected. Up to 50 percent of the total resin capacity can be loaded with the chromatographic mixture to be separated.

The instant invention also encompasses an apparatus for separating at least two chromatographic species from each other in accordance with the above-described method. The apparatus comprises a particulate bed containing a resin. Means are provided for simultaneously introducing the feed mixture stream, the displacer reagent stream, and the barrier reagent stream proximate one end of the particulate bed. In addition, means are provided for moving the stream with respect to the particulate bed so that substantially all the resin is sequentially contacted with (i) the feed mixture stream, (ii) the displacer reagent stream, and (iii) the barrier reagent stream.

DRAWINGS

These and other features, aspects, and advantages of the present invention will become better understood with reference to the following description, appended claims, and accompanying drawings where:

DETAILED DESCRIPTION OF THE INVENTION

The present invention is directed to (a) a continuous displacement chromatographic method and (b) an apparatus for use therein.

Figure 1:
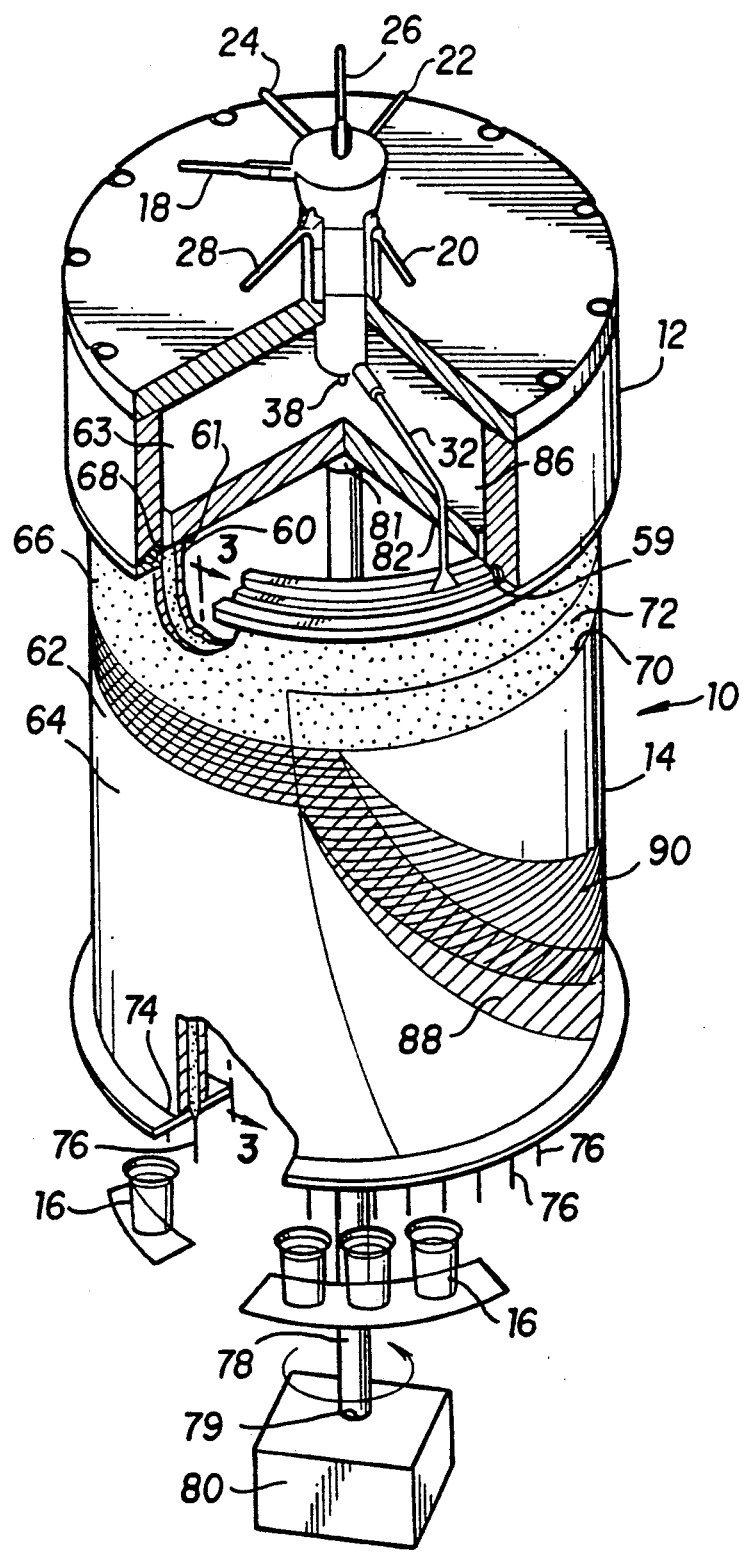
FIG. 1 is a perspective view of a continuous chromatographic apparatus embodying features of the instant invention.
Figure 2:
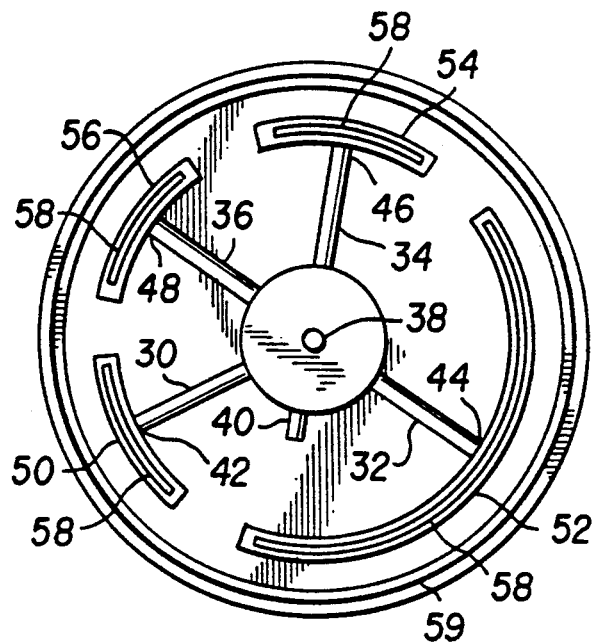
FIG. 2 is a bottom plan view of the top manifold of the apparatus of FIG. 1.
Figure 3:
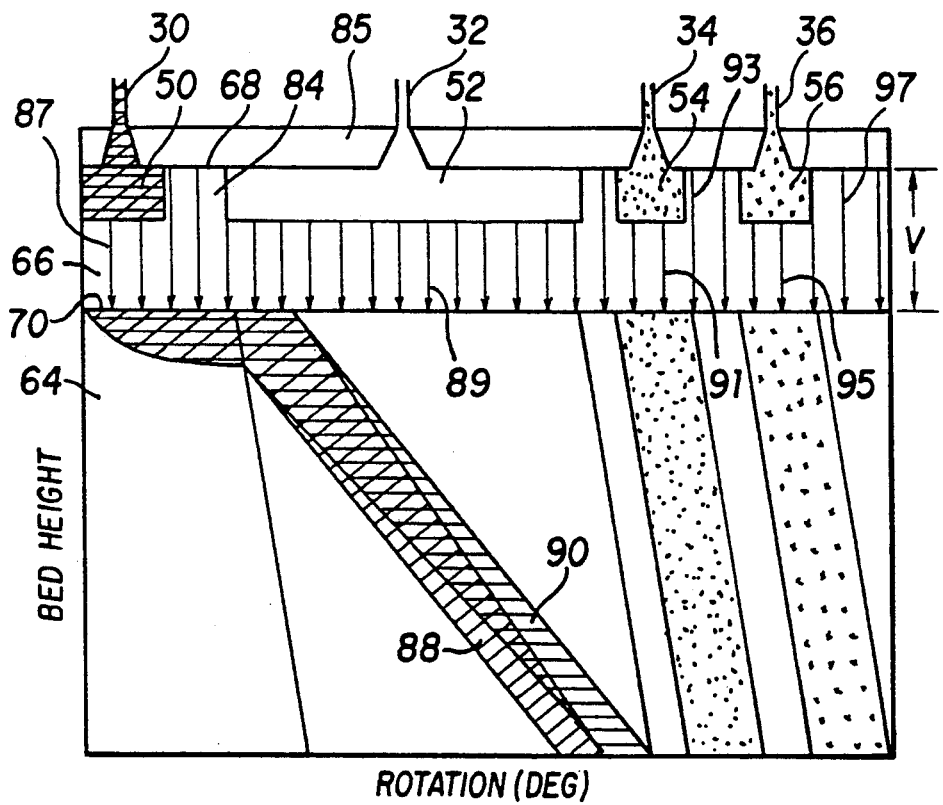
FIG. 3 is a two-dimensional sectional view along lines 3—3 of FIG. 1 showing the distribution of various reagent sectors in a continuous chromatographic separation method embodying features of the present invention.

With reference to the Figures, the present invention as shown in FIGS. 1-3 provides a continuous displacement chromatographic (CDC) apparatus 10 for use in a CDC method. The apparatus 10 comprising a stationary inlet distributor manifold 12, a rotating annular particulate bed 14, and a plurality of stationary collector receptacles 16. The stationary inlet distributor 12 comprises a plurality of inlet tubes 18–28 and a corresponding plurality of distribution tubes 28–38. In particular, the stationary inlet distributor 12 has a feed mixture inlet tube 18, a displacer reagent inlet tube 20, a regenerator reagent inlet tube 22, a barrier reagent inlet tube 24, a purge inlet tube 26, and an inert gas over-pressure inlet tube 28 as well as corresponding distribution tubes, namely, a feed mixture distribution tube 30, a displacer reagent distribution tube 32, a regenerator reagent distribution tube 34, a barrier reagent distribution tube 36, a purge distribution tube 38, and an inert gas over-pressure distribution tube 40, respectively. The exit ends 42, 44, 46, and 48 of the feed mixture distribution tube 30, the displacer reagent distribution tube 32, the regenerator reagent distribution tube 34, and the barrier reagent distribution tube 36, respectively, each preferably terminate in a device 50, 52, 54, and 56, respectively, adapted to distribute its respective mixture or reagent over a sector having a greater area than the cross-sectional area of its respective distribution tube 30, 32, 34, and 36. As shown in FIG. 2, each distribution device 50, 52, 54, and 56 can terminate in an elongated slot 58. Alternatively, one or more of the distribution devices 50, 52, 54, and 56 can terminate in a series of nozzles (not shown).

The stationary inlet distributor manifold 12 is in O-ring sealed contact 59 with the rotating annular particulate bed 14. The O-ring seal 59 enables axial rotation of the inlet distributor manifold 12 relative to the annular particulate bed 14. The rotating annular particulate bed 14 is defined by a cylindrical inner core 60 and a coaxial cylindrical exterior shell 62. Sandwiched between the inner core 60 and the exterior shell 62 is a resin 64. The annular thickness between the inner core 60 and the exterior shell 62 can be almost as large as the radius of the exterior shell 62. For example, the annular thickness can be such that the resin 64 occupies up to about 95% of the cross-sectional area of the exterior shell 62.

A chromatographically inert retaining layer 66 is also sandwiched between the core 60 and shell 62 in the space V (see FIG. 3) between the top 68 of the rotating annular particulate bed 14 and the upper edge 70 of the resin 64. At least a portion of each distribution device 50, 52, 54, and 56 is submerged in the inert retaining layer 66. The depth of the chromatographically inert retaining layer 66 is sufficient to prevent substantially any disruption of the resin 64 due to the introduction of the feed mixture or various reagents through the distributor devices 50, 52, 54, and 56. An exemplary chromatographically inert retaining layer 64 is comprised of glass beads 72. Preferably, the glass beads 72 have a particle size sufficiently small so that the distributor devices 50, 52, 54, and 56 are capable of horizontally passing through the glass beads 72 without any significant impedance.

The top 61 of the inner core 60 is capped with an upwardly-pointing, conically-shaped cover plate 63 having a diameter substantially the same as the outer-diameter of the inner core 60. The lower portion 74 of the particulate bed 14 terminates in a plurality of exit tubes 76. The annular particulate bed 14 is rotated by a coaxial shaft 78 having one end 79 attached to a motor 80 and another end 81 attached to the lower surface 82 of the cover plate 63.

In accordance with a method embodying features of the instant invention, a feed mixture stream, a displacer reagent stream, a regenerator reagent stream, a barrier reagent stream, and a purge reagent stream are simultaneously fed into the apparatus 10 through the feed mixture inlet tube 18, the displacer reagent inlet tube 20, the regenerator reagent inlet tube 22, the barrier reagent inlet tube 24, and the purge inlet tube 26, respectively, of the stationary inlet distributor manifold 12. The feed mixture stream comprises chromatographic species B and C wherein C has a greater affinity than B for the resin 64. The displacer reagent stream comprises a chromatographic specie D wherein D has a greater affinity than C for the resin 64. The regenerator reagent stream is capable of displacing D from the resin 64 without otherwise substantially effecting the resin 64. In one version of the instant invention, the regenerator reagent stream contains a composition, e.g., a chelating agent, that has a greater affinity for D than the affinity of D for the resin 64. In another version of the instant invention, the regenerator reagent stream has a pH capable of removing D from the resin 64. The barrier reagent stream comprises a chromatographic specie A having a lesser affinity than B for the resin 64.

The feed mixture stream, the displacer reagent stream, the regenerator reagent stream, and the barrier reagent stream exit the inlet distributor manifold 12 simultaneously through the feed distribution device 50, the displacer distribution device 52, the regenerator distribution device 54, and the barrier distribution device 56, respectively. These streams separately enter the chromatographically inert retaining layer 66 and proceed downwardly into the resin 64. The purge stream exits the inlet distributor manifold 12 through the purge stream distribution tube 38 and impinges upon the center of the upper surface 86 of the conically-shaped cover plate 63. The purge stream runs down over the upper surface 86 of the cover plate 63 substantially equally in all directions and enters the chromatographically inert retaining layer 66 at those points not occupied by either the feed stream or one of the reagent streams. The purge stream remains substantially distinct from the feed stream and each of the reagent streams as it passes through the retaining layer 66 and enters the resin 64. To prevent any disruption in the steady state nature of the CDC method of the instant invention, it is preferred that all streams be introduced through the stationary inlet distributor manifold 12 at substantially the same flux rate (volume/time/area).

When an inert over-pressure gas is used to expedite the CDC process, pressurizing gas enters the stationary inlet distributor 12 through the pressurizing gas inlet tube 28 and exits through the pressurizing gas distribution tube 40 located above the upper surface 86 of the conically-shaped cover plate 63.

Initially, the resin 64 is loaded with chromatographic specie A. In one version of the invention, chromatographic specie A is loaded onto the resin 64 prior to the resin 64 being placed in the particulate bed 14. However, in the preferred version of the invention, chromatographic specie A is loaded onto the resin 64 by first passing only the barrier reagent stream through the barrier distribution device 56 and through the resin 64 until substantially 100 percent of the resin's binding capacity is occupied by chromatographic specie A.

As shown in FIG. 1, the particulate bed 14 is rotated counterclockwise. Accordingly, chromatographic specie A is displaced from the resin 64 by chromatographic species B and C in the feed mixture stream passing through the feed distribution device 50. The feed mixture stream is introduced over a sector that generally spans at least about 5° (or at least about 1 percent of the horizontal cross-sectional area of the particulate bed 14). More typically, the feed mixture stream is introduced over a sector of about 10° to about 20° ( or about 3 to about 6 percent of the horizontal cross-sectional area of the particulate bed 14).

Generally, sufficient feed mixture stream is introduced in the resin 64 so that up to about 50 percent of the total resin capacity is occupied by chromatographic species B and C. Typically, at least about 5 percent of the total resin capacity of the resin 64 is occupied by chromatographic species B and C. Since the amount of chromatographic species capable of being separated is directly proportional to the total binding capacity of the resin 64, it is preferred that the chromatographic species to be separated occupy as much of the resin's binding capacity as is consistent with displacement chromatography principles. For example, it is preferred that the chromatographic species to be separated occupy at least about 40%, and more preferably at least about 45%, of the resin's binding capacity.

In a preferred version of the invention, it is preferred that the particulate bed 14 be rotated about 360° with only the feed stream being introduced into the resin 64 through the feed distribution device 50. To remove substantially all chromatographic species displaced by the feed mixture, e.g., displaced A, it is preferred, as shown in FIG. 3, that a portion 84 of the purge stream 85 emanating from the purge stream distribution tube 38 be introduced into the resin 64 between the feed mixture stream 87 and the displacer reagent stream 89. The displacer reagent stream 89, which is introduced into the resin 64 through the displacer distribution device 52, contains chromatographic specie D having a greater affinity than chromatographic species B and C for the resin 64. Accordingly, chromatographic specie D displaces chromatographic species B and C from the resin 64. In order to substantially, fully separate specie B from specie C, it is preferred that displacer specie D be introduced over a sector having a horizontal length at least as long as the minimum critical batch column length (i.e., "band length" in displacement chromotography terms) necessary to resolve specie B from specie C. The band length is the length of a batch column initially occupied by the feed mixture prior to introducing the displacer into the batch column. Typically, the displacer specie D is introduced over a sector of at least about 120° (or at least about 33 percent of the horizontal cross-sectional area of the particulate bed 14). Preferably, D is introduced over a sector that spans at least about 180° (or at least about 50 percent of the horizontal cross-sectional area of the particulate bed 14).

Due to their differing chromatographic affinities for the resin 64, chromatographic specie C displaces chromatographic specie B as they traverse the resin 64 and form distinct, adjacent bands 88 and 90 containing substantially pure B and C, respectively. Chromatographic species B and C substantially separately pass through their adjacent, respective exit tubes 76 and are substantially separately collected at the lower portion 74 of the rotating annular particulate bed 14 in separate stationary collector receptacles 16. The displacer chromatographic specie D is removed from resin 64 the regenerator stream 91 emanating from a regenerator distribution device 54. The regenerator stream is usually introduced into the particulate bed 14 over a sector of at least about 35° (or at least about 10 percent of the horizontal cross-sectional area of the particulate bed 14). More typically, the regenerator stream is introduced over a sector of about 35° to about 100° (or about 10 to about 30 percent of the horizontal cross-sectional area of the particulate bed 14).

The regenerator stream 91 is in turn removed from the resin 64 by another portion 93 of the purge stream 85. Chromatographic barrier specie A is then reloaded onto the resin 64 by the barrier reagent stream 95 emanating from the barrier distribution device 56. The barrier stream is also usually introduced into the particulate bed 14 over a sector of at least about 35° (at least about 10 percent of the horizontal cross-sectional area of the particulate bed 14). However, the barrier stream is more typically introduced over a sector of about 35° to about 100° (or about 10 to about 30 percent of the horizontal cross-sectional area of the particulate bed 14). Any unbound chromatographic specie A is removed from the resin 64 by a further branch 97 of the purge stream 85. After removing any excess chromatographic specie A, the particulate bed 14 is substantially in the same condition as it was at the beginning of the cycle. The cycle can be repeated as many times as necessary and, therefore, the process is continuous. Typically, the cycle is repeated at least twice.

As evident from the above discussion and as illustrated in FIG. 3, iy is preferred that the feed mixture stream and each reagent stream be separated from its neighboring reagent stream or feed mixture stream by the purge stream 85. However, satisfactory results are also obtainable when various neighboring streams are not separated by the purge stream 85.

Figure 4:
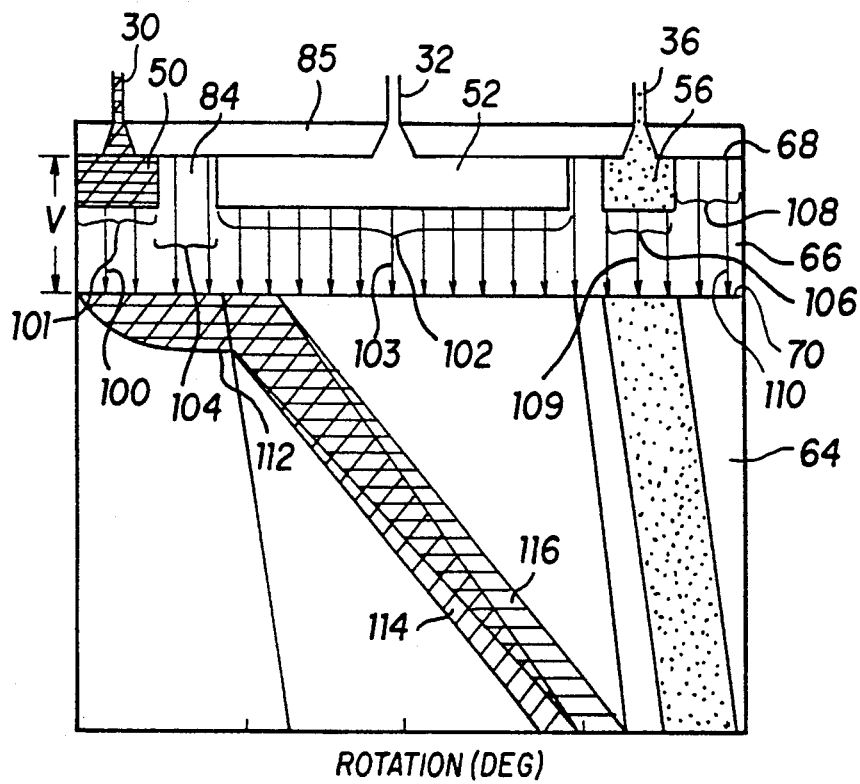
FIG. 4 is a two-dimensional representation of the distribution of various reagent sectors in a continuous chromatographic separation method embodying features of the present invention as detailed in the Example.

In one version of the invention, the barrier and regenerator reagent streams act in the same manner and can be combined into a single reagent stream as illustrated in FIG. 4 and discussed in the Example, infra.

The sectors for the feed mixture stream, the displacer reagent stream, the regenerator reagent stream, the barrier reagent stream, and each portion of the purge stream can be varied in accordance with their concentrations, flux rates, and constituents. However, in all cases, it is preferred that the displacer stream sector be as large as possible so that the maximum amount of chromatographic species can be separated per cycle.

Any displacement chromatographic method capable of being performed by a batch process can now be performed continuously by the CDC method of the instant invention. Exemplary chromatographic methods include liquid-liquid, liquid-solid, ion-exchange, size-exclusion, bonded-phase, and ion-pair chromatography methods. Any organic or inorganic compound capable of being separated by a batch displacement chromatographic method can be separated continuously by the CDC method of the instant invention. As used in the specification and claims, the term "organic compound" means any compound containing at least one carbon atom and the term "inorganic compound" means any compound devoid of even one carbon atom. Exemplary organic compounds that can be separated continuously by the CDC method of the instant invention include, but are not limited to, drugs, proteins, antibodies, enzymes, and organometallic compounds. Exemplary inorganic compounds that can be separated continuously by the CDC method of the instant invention include, but are not limited to, transition metals, lanthanides, actinides, and minerals.

Accordingly, the instant invention is capable of continuously separating large quantities of chromatographic species per unit volume of resin 64.

EXAMPLE

Overview

The separation of rare earth elements is described in the following example.

Materials

A stock solution containing about 150 g/l each of neodymium (Nd) and praseodymium (Pr) was prepared using neodymium carbonate (about 96.0% $Nd_2(CO_3)_3$) and praseodymium oxide (about 96.0% min $Pr_6O_{11}$).

Neodymium carbonate (about 248.7 g) was dissolved in about 300 ml water containing about 67 ml of about 70% nitric acid. Incremental addition of the carbonate was carried out to prevent loss of material during effervescence. Praseodymium oxide (about 187.1 g) was dissolved in about 100 ml of hot 70% nitric acid. Incremental addition of the oxide to the hot acid was followed by frequent dropwise addition of about 30% hydrogen peroxide to reduce Pr(4+) to the Pr(3+) oxidation state. Following complete dissolution, the Pr mixture was boiled to a viscous state to expel excess nitric acid and rediluted by carful addition of water. The solution was then brought to approximately 450 ml total volume, with addition of about 0.5 ml of about 70% nitric acid to prevent hydroxide formation. After cooling to room temperature, the two solutions were combined and diluted to a final volume of about 1000 ml. Nd/Pr feed solutions for displacement chromatography experiments were prepared by dilution of the stock solution.

The displacer reagent employed was an aqueous solution (about 5 g/l) of N-(2-hydroxyethyl)ethylenediamine-triacetic acid (HEDTA) in the ammonium ion form (which as a chelating agent complexes with i.e., modifies, B and C, such that in their complexed, i.e., modified forms, they have less affinity for this resin). HEDTA was dissolved in water and the pH was adjusted to about 7.5 using aqueous ammonium hydroxide.

The resin used in the annular chromatograph experiments was Dowex 50W-X8 brand (about 44–74 micron) sulfonated polystyrene-divinyl benzene cation exchange resin.

All other reagents employed were of analytical grade. All solutions were prepared using deionized water further purified with a Barnstead NANOpure brand water purifier.

Apparatus

A 27.9 cm diameter by 60 cm overall length continuous annular chromatograph with a 12.7 mm wide annulus was employed in this study.

Flow rates for feeds and eluents were controlled by metering pumps to within about 1%.

A Perkin-Elmer Model 354 brand UV/Vis Spectrophotometer was used for optical determination of the concentrations of ammonium HEDTA solutions of Nd(3+) (578 nm) and Pr(3+) (444 nm). The millivolt signals from the detector were converted to digital signals by an A/D conversion board (Data Translation Model 2801) interfaced to an IBM-AT brand personal computer for graphical display and digital data storage.

Nd and Pr concentrations were also determined using a Perkin-Elmer Model 2380 brand Atomic Absorption (AA) Spectrophotometer, Nd (492.4 nm) and Pr (495.1 nm), and an Applied Research Laboratories Model 3520 brand Sequential Inductively Coupled Plasma atomic Emission Spectrometer (ICP-AES), Nd (404.079 nm) and Pr (440.878 nm).

Methods

An Nd/Pr binary lanthanide mixture was selected to demonstrate the concepts because Nd/Pr represented a separation of adjacent lanthanides that could be monitored visually (Nd(3+) is purple and Pr(3+) is green).

Sulfonated polystyrene-divinylbenzene cation exchange resin was used as the stationary resin phase. An aqueous solution (about 5 g/l) of HEDTA in the ammonium ion form at pH about 7.5 served as the displacer D and hydrogen ion (H+) was used as the barrier ion A.

The annular chromatograph was loaded with resin to a depth of about 22.8 cm and topped with a layer (about 10 cm) of inert glass beads (about 0.18 mm diameter). The stationary inlet distributor manifold 12 delivery system was configured to enable the introduction of feed, displacer, barrier, and purge water to fixed locations around the top of the chromatograph.

Each distribution tube terminated in a separate series of nozzles that penetrated beneath the surface of the glass bead layer but not to the extent of penetrating the top of the resin. As the particulate bed rotated, the glass beads flowed around the stationary nozzles so as not to disturb the surface of the actual resin. The glass beads, however, served to prevent lateral upward diffusion and mixing of the different reagent streams at the top of the chromatograph. This enabled the introduction of reagents to different sectors around the top of the chromatograph in discrete, well defined regions.

The particulate bed operated in a manner to exclude all but the reagent issuing from an individual series of distribution tube nozzles from the region directly below those nozzles. The widths of each of the different reagent sectors could be varied by varying the widths of each individual series of distribution nozzles. The sequence of addition of feed, displacer, barrier, and purge around the circumference of the chromatograph could also be varied.

As shown in FIG. 4, in the experiment described below, the Nd/Pr feed 100 was introduced at a fixed position (0 degrees) in a 15 degree sector 101. This was followed by a sector 102 (about 195 degrees) containing the HEDTA displacer 103. (Note: some space 104 was allowed between the feed and displacer nozzles to prevent acid displaced by the loaded feed from entering the ammonium HEDTA displacer sector 102). A barrier sector 106 and a purge sector 108 containing about 0.1 N nitric acid 109 and deionized water 110, respectively, made up the remainder of the circumference, with each of these sectors 106 and 108 being about 75 degrees wide.

All the resin 64 in the particulate bed was first converted to the H+ form and then purged with water to remove excess acid before beginning a run. This was conveniently accomplished by feeding reagent through purge distribution tube 38 centered in the head space above the chromatograph that fed radially to all portions of the chromatograph. This included the sectors below any distribution nozzles not concurrently in use. Deionized water was then applied to the purge distribution tube 38 for the remainder of a separation.

With the chromatograph rotating at 25.5° /hour, a separation was initialized by first applying the feed mixture 100 to the particulate bed at a flow rate of about 7.2 ml/minute. This was then followed by the addition of the displacer reagent 103 (at a flow rate of about 130 ml/minute), the barrier reagent 109 (at a flow rate of about 37 ml/minute), and purge water 110 through their separate distribution nozzles, in that order and at substantially the same flux rate. The various flow rates were adjusted according to the particular conditions in a given experiment. Once suitable steady-state operating conditions were established, the separations could be sustained continuously for an indefinite period.

The progress of a continous separation could be monitored and the resulting chromatograms recorded by attaching a slip-stream to a single exit tube 76 at the bottom of the chromatograph and analyzing the eluate as the exit tube 76 rotated the entire 360 degrees of the chromatograph circumference. Continuous, in-line detection and monitoring was, in this manner, conveniently accomplished.

The continuous CDC separations were conducted at room temperature.

Results and Discussion

As indicated above, a 15 degree feed sector or region 101 followed by a 195 degree ammonium HEDTA displacer sector 102 and two 75 degree sectors 106 and 108 containing the acid regenerator 109 and water purge 110, respectively, were employed for the Nd/Pr separation under consideration.

With the entire resin initially in the hydrogen ion form and with deionized water flowing to the purge distribution tube 38, the Nd/Pr feed 100 was applied to the rotating particulate bed at a concentration of about 10 g/l in each metal. In the absence of displacer reagent 103, the 3+ lanthanides adhered strongly to the resin and accumulated in a narrow band 112 at the top of the rotating resin.

This was followed by the ammonium HEDTA displacer sector 102 at a concentration of about 5 g/l and pH about 7.5, which resulted in a fixed region of displacer in the particulate bed into which the feed mixture entered. Separation and development of the individual component bands of the Nd 114 and Pr 116, occurred in this region.

The length of the particulate bed was adjusted to allow for complete separation to develop before material exited the chromatograph. This length was determined from the flow rate and concentration of feed 100 applied to the resin, the flow rate and concentration of the ammonium HEDTA displacer 103, and the extent of the reagent sectors 102 and 106. Once separation into adjacent bands 114 and 116 and a steady-state condition was achieved, additional resin depth would provide no further improvement in separation in the displacement experiment. This is referred to as the "isotactic" point in displacement chromatography.

An acid regenerator sector 106 (about 0.1 N nitric acid) was required after the ammonium HEDTA displacer sector 102 to convert the resultant ammonium ion form of the resin back to the initial hydrogen ion form. Excess acid from the regenerator sector 106 was swept from the resin before returning to the feed sector 101 by a final deionized water purge 110. This restored the resin 64 to its initial conditions and enabled continuous operation.

Figure 5:
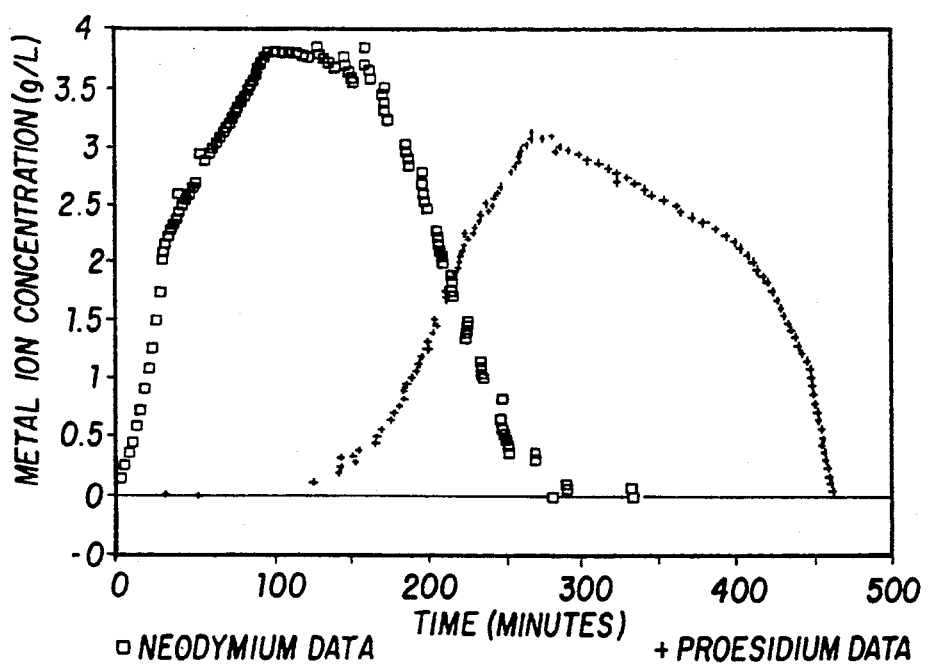
FIG. 5 is a chromatogram of the continuous displacement chromatographic separation experiment of the Example.

A chromatogram obtained during this experiment is shown in FIG. 5. The curves indicated displacement chromatographic behavior. The separated components appeared as adjacent bands of approximately equal concentrations and areas. Displacement chromatography was, therefore, being accomplished continuously with the procedure and apparatus of the instant invention.

Although the present invention has been described in considerable detail with reference to several preferred versions thereof, other versions are possible. For example, the feed mixture stream can contain more than two chromatographic species to be separated. In addition, the inlet distributor manifold can be rotated while the particulate bed is held substantially stationary, and the rotation can be in either the clockwise or counterclockwise direction. Furthermore, the particulate bed need not be annular. To illustrate, the particulate bed can be linear and the various inlet tubes can be moved continuously over the top portion of the linear particulate bed. Also, instead of having an annular slot, the distribution device can have an opening that is wedge-shaped. Therefore, the spirit and scope of the appended claims should not necessarily be limited to the description of the preferred versions contained herein.

What is claimed is:

1. A method for separating at least two chromatographic species from each other, the method comprising the steps of:
   (a) simultaneously introducing a feed mixture stream, a displacer reagent stream, and a barrier reagent stream proximate a first end of a particulate bed, the particulate bed comprising a resin, the feed mixture stream comprising chromatographic species B and c wherein C has a greater affinity than B for the resin, the displacer stream comprising a specie D wherein D modifies B and C such that their modified forms have less affinity for the resin, and the barrier stream comprises a chromatographic specie A wherein A has a lesser affinity than B for the resin;
   (b) moving the streams with respect to the particulate bed so that substantially all the resin is sequentially contacted with (i) the feed mixture stream, (ii) the displacer reagent stream, and (iii) the barrier reagent stream;
   (c) collecting substantially pure B; and
   (d) collecting substantially pure C.

2. The method of claim 1 wherein substantially all the resin is at least twice sequentially contacted with (i) the feed mixture stream, (ii) the displacer reagent stream, and (iii) the barrier reagent stream.

3. The method of claim 1 wherein the method further comprises the step of loading the resin with A prior to step (a).

4. The method of claim 1 wherein step (a) includes the step of simultaneously introducing a purge stream proximate the first end of the particulate bed and step (b) includes the step of moving the streams with respect to the particulate bed so that substantially all the resin is sequentially contacted with (i) the feed mixture stream, (ii) the displacer reagent stream, (iii) the barrier reagent stream, and (iv) the purge stream.

5. The method of claim 4 wherein step (b) includes the step of moving the streams with respect to the particulate bed so that substantially all the resin is sequentially contacted with (i) the feed mixture stream, (ii) the purge stream, (iii) the displacer reagent stream, (iv) the barrier reagent stream, and (v) the purge stream.

6. The method of claim 4 wherein the purge stream is water.

7. The method of claim 1 wherein the streams are held substantially fixed and the particulate bed is rotated.

8. The method of claim 1 wherein the particulate bed is held substantially fixed and the streams are simultaneously rotated.

9. The method of claim 1 wherein step (a) includes the step of simultaneously introducing a regenerator reagent stream proximate the first end of the particulate bed and step (b) includes the step of moving the streams with respect to the particulate bed so that substantially all the resin is sequentially contacted with (i) the feed mixture stream, (ii) the displacer reagent stream, (iii) the regenerator reagent stream, and (iv) the barrier reagent stream.

10. The method of claim 1 wherein step (a) includes the step of simultaneously introducing a regenerator reagent stream and a purge stream proximate the first end of the particulate bed and step (b) includes the step of moving the streams with respect to the particulate bed so that substantially all the resin is sequentially contacted with (i) the feed mixture stream, (ii) the displacer reagent stream, (iii) the regenerator reagent stream, (iv) the barrier reagent stream, and (v) the purge stream.

11. The method of claim 10 wherein step (b) includes the step of moving the streams with respect to the particulate bed so that substantially all the resin is sequentially contacted with (i) the feed mixture stream, (ii) the purge stream, (iii) the displacer reagent stream, (iv) the regenerator stream, (v) the barrier reagent stream, and (vi) the purge stream.

12. The method of claim 1 wherein B and C are selected from the group consisting of organic and inorganic compounds.

13. The method of claim 1 wherein step (a) includes introducing the feed mixture stream proximate the first end of the particulate bed over the zone that spans about 3 to about 6 percent of the horizontal cross-sectional area of the particulate bed.

14. The method of claim 1 wherein step (a) includes introducing the displacer reagent stream proximate the first end of the particulate bed over the zone that spans at least about 33 percent of the horizontal cross-sectional area of the particulate bed.

15. The method of claim 1 wherein step (a) includes introducing the barrier reagent stream proximate the first end of the particulate bed over the zone that spans at least about 10 percent of the horizontal cross-sectional area of the particulate bed.

16. The method of claim 1 wherein step (a) includes the step of loading the resin with the feed mixture stream so that B and C occupy about 5 to about 50 percent of the total resin capacity.

17. The method of claim 1 wherein step (a) includes introducing all the streams at substantially the same flux rate.

18. The method of claim 1 wherein step (a) includes the step of introducing the feed mixture stream, the displacer reagent stream, and the barrier reagent stream into a chromatographically inert retaining layer and then through the resin.

19. A method for separating at least two chromatographic species from each other, the method comprising the steps of:
(a) loading a particulate bed with a chromatographic specie A, the particulate bed comprising a resin;
(b) simultaneously introducing a feed mixture stream, a displacer reagent stream, a barrier reagent stream, and a purge stream into a chromatographically inert retaining layer and then through the resin, the feed mixture stream comprising chromatographic species B and C wherein C has a greater affinity than B for the resin, the displacer reagent stream comprising a specie D wherein D forms chelate complexes with B and C which complexes have little affinity for the resin, and the barrier reagent stream comprises a chromatographic specie A wherein A has a lesser affinity than B for the resin;
(c) moving the streams with respect to the particulate bed so that substantially all the resin is at least twice sequentially contacted with (i) the feed mixture stream, (ii) the displacer reagent stream, (iii) the barrier reagent stream, and (iv) the purge stream;
(d) collecting substantially pure B; and
(e) collecting substantially pure C.

20. A method for separating at least two chromatographic species from each other, the method comprising the steps of:
(a) loading a particulate bed comprising a resin with a chromatographic specie A so that substantially all of the resin is loaded with A;
(b) displacing at least a portion of A from the resin with a mixture of at least two chromatographic species that are to be substantially separated from each other, each of the chromatographic species to be separated having a greater affinity than A for the resin;
(c) simultaneously introducing a stream of chromatographic specie A, a stream of the mixture of chromatographic species to be separated, and a stream of a chromatographic specie D proximate a top portion of the resin bed, wherein D modifies all of the chromatographic species to be separated in such a way that their modified forms have little affinity for the resin;
(d) moving the stream of A, the stream of the mixture of the chromatographic species to be separated, and the stream of D with respect to the particulate bed so that substantially all the resin is sequentially contacted with (i) the species to be separated, (ii) D, and (iii) A; and
(e) substantially separately collecting each chromatographic specie in the mixture.

* * * * *

UNITED STATES PATENT AND TRADEMARK OFFICE
CERTIFICATE OF CORRECTION

PATENT NO. : 5,149,436

DATED : September 22, 1992

INVENTOR(S) : Vernon T. Taniguchi and Allen W. Doty

It is certified that error appears in the above-identified patent and that said Letters Patent is hereby corrected as shown below:

On title page, item [56], "OTHER PUBLICATIONS"
    Page 2, column 2, replace "Streat" with -- Byers, C. H.
    et al., --

Claim 1, column 12, line 10, replace "c" with -- C --.

Signed and Sealed this

Fifth Day of October, 1993

*Attest:*

BRUCE LEHMAN

*Attesting Officer*     *Commissioner of Patents and Trademarks*